United States Patent [19]

Noonan, Jr.

[11] Patent Number: 4,521,171
[45] Date of Patent: Jun. 4, 1985

[54] FOOT PATTERN DEVICE

[76] Inventor: David Noonan, Jr., 227 Linden St., Manchester, N.H. 03104

[21] Appl. No.: 594,322

[22] Filed: Mar. 28, 1984

[51] Int. Cl.³ .............................................. B29C 17/00
[52] U.S. Cl. ........................................ 425/2; 425/394; 425/DIG. 48
[58] Field of Search .................. 425/2, 119, 388, 394, 425/398, 400, DIG. 48, DIG. 57

[56] References Cited

U.S. PATENT DOCUMENTS

| | | | |
|---|---|---|---|
| Re. 25,484 | 11/1963 | Kostur | 425/388 X |
| 2,082,451 | 6/1937 | Kivlahan et al. | 425/2 |
| 2,333,481 | 11/1943 | Limmer | 425/2 |
| 2,440,508 | 4/1948 | Gould | 425/2 X |
| 2,694,227 | 11/1954 | Fordyce et al. | 425/388 X |
| 2,740,143 | 4/1956 | Frieri | 425/119 X |
| 3,179,980 | 4/1965 | Ryan et al. | 425/388 |
| 3,188,687 | 6/1965 | Blair | 425/388 X |
| 3,317,960 | 5/1967 | Kramer | 425/DIG. 48 |
| 3,319,295 | 5/1967 | Jones-Hinton et al. | 425/DIG. 48 |
| 3,458,898 | 8/1969 | Easparis | 425/2 |
| 3,659,991 | 5/1972 | Diamond | 425/DIG. 48 |
| 3,744,262 | 7/1973 | Bose | 425/388 X |
| 3,841,819 | 10/1974 | Diamond | 425/DIG. 48 |
| 4,157,884 | 6/1979 | Andrae | 425/388 X |
| 4,252,518 | 2/1981 | Kiefer | 425/398 X |
| 4,470,782 | 9/1984 | Zimmerman | 425/2 |

FOREIGN PATENT DOCUMENTS 908098  10/1962  United Kingdom ....... 425/DIG. 48

Primary Examiner—J. Howard Flint, Jr.
Attorney, Agent, or Firm—Joseph S. Iandiorio; William E. Noonan

[57] ABSTRACT

A foot pattern device including: a cavity having a base and a wall portion; a foot form in the cavity on the base; a frame releasably securable to the base for gripping a deformable sheet between the lower edge of the frame and the upper part of the wall portion; means for heating the deformable sheet; and clamp means for holding the frame tightly to the wall portion with the deformable sheet between them as the foot is pressed on the warm deformable sheet into the foot form.

5 Claims, 8 Drawing Figures

1

FOOT PATTERN DEVICE

FIELD OF INVENTION

This invention relates to a foot pattern device for forming a mold of a foot.

BACKGROUND OF INVENTION

It is often necessary to make a mold of a foot for the purpose of making a prosthetic device or insert for a shoe. One conventional technique uses Plaster of Paris or similar material, usually combined with a wrapping material, to form an impression of the foot from which a positive replica can be made. This is a slow process, is generally messy and the cast is removed only with careful, tedious effort. In other approaches, wax or various plastics are used by applying heat to them in one step or device and then carrying out the forming in a second. In applications using plaster, wax or cork, if the mold is crushed it cannot be recovered but must be re-molded. Some molding techniques require pressure levels while molding, which temporarily deform the foot and produce unsuitable reproductions.

SUMMARY OF INVENTION

It is therefore an object of this invention to provide an improved foot pattern device for quickly and easily making a mold of a foot.

It is a further object of this invention to provide such a device which makes a mold of a foot cleanly and neatly without any mess.

It is a further object of this invention to provide such a device which is non-crushable yet can be reheated for re-molding should the first mold attempt be unsatisfactory.

It is a further object of this invention to provide such a device which has all of the necessary parts including heating, holding and molding parts in a single unit.

The invention features a foot pattern device including a cavity having a base and a wall portion. There is a foot form in the cavity on the base and a frame is releasably securable to the base for gripping a deformable sheet between the lower edge of the frame and the upper part of the wall portion. There are means for heating the deformable sheet and clamp means for holding the frame tightly to the wall portion with the deformable sheet between them as a foot is pressed on the warm deformable sheet into the foot form.

In a preferred embodiment, the frame is hingeably connected along one edge to the wall portion and there is a housing for slidably receiving the cavity and frame. The heating means may be disposed in the housing and there may be provided on either or both the lower edge of the frame and the upper edge of the wall portion, where they meet, a high-friction material for gripping the deformable sheet.

DISCLOSURE OF PREFERRED EMBODIMENT

Other objects, features and advantages will occur from the following description of a preferred embodiment and the accompanying drawings, in which.

2

Figure 2:
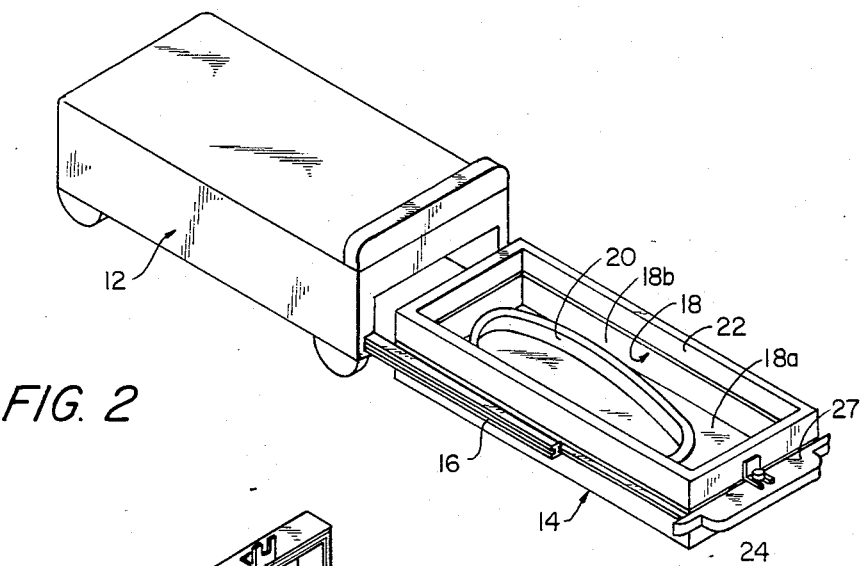
FIG. 2 is a view similar to FIG. 1 with the cavity and frame withdrawn from the housing.
Figure 4:
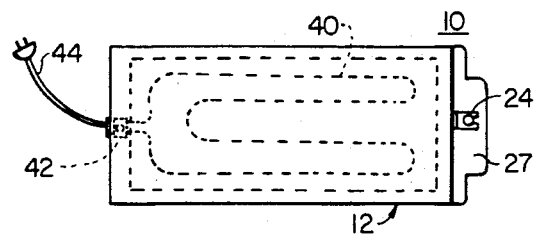
Figure 5:
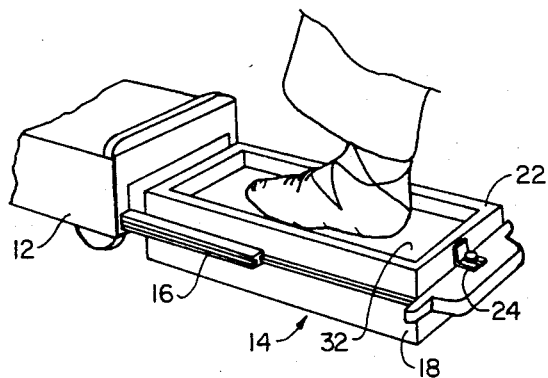
Figure 6:
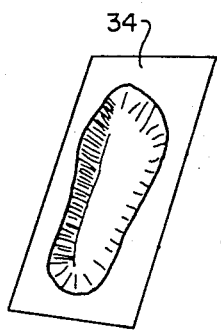

FIG. 4 is a schematic top plan view showing the location of the heater;

FIG. 5 is a view similar to FIG. 2 with the deformable sheet mounted between the frame and cavity;

FIG. 6 is a view of a foot mold made with the device of this invention; and

Figure 7A:
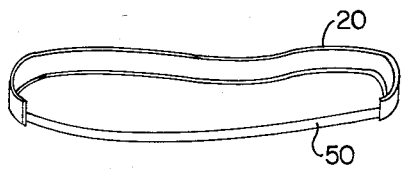
Figure 7B:
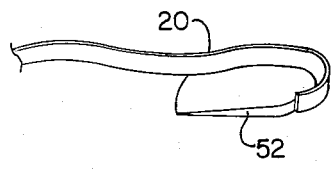

FIGS. 7A and 7B are alternative construction of the device for compensating for specific peculiarities.

The foot pattern device of this invention may be accomplished with a cavity having a base and wall portion both of which may be made out of wood or similar materials sufficiently rugged to take the weight of a person's foot and to withstand the mild heating required to soften the plastic sheet, e.g., the aluminum and molded plastic. In the cavity on the base is a foot form which is made in the generalized outline of a foot and usually having a height no greater than or only slightly greater than the wall portion of the cavity. There is an open frame releasably securable to the base for gripping a deformable sheet between the lower edge of the frame and the upper part of the wall portion. The frame is typically made out of the same material as the cavity, for example wood, and may be hinged at one end so that it can swing up and away from the cavity to allow a sheet of heat-deformable material such as acetate or polystyrene plastic to be secured. The frame is swung up to insert the sheet and then swung back down to a clamped position to hold the sheet tightly in place. The outside of the base includes two runners which are interconnected with a housing which is typically made of the same material, e.g. wood, as the cavity and frame. The runners allow the cavity and frame to be slid into the housing, where a heater, such as a 110-volt, approximately 1000-watt heater, is located under the top surface. When the cavity and frame with the plastic sheet in place is in the housing the heater is switched on for a short period of time, e.g. approximately ninety seconds, until the plastic sheet is warmed to a deformable point. The heater is then switched off, the cavity and frame are withdrawn from the housing, and the patient is directed to place his foot on top of the sheet over the foot form and press downwardly to make the mold. To increase the holding ability of the clamping action of the frame and cavity, a high-friction material, such as foam rubber, may be adhered to the upper portion of the wall and/or the lower portion of the frame where they meet. In particular cases it may be desirable to place inserts of various shapes within the foot form to intentionally introduce a change in the mold to accommodate a particular deformity or affliction of the patient.

Figure 1:
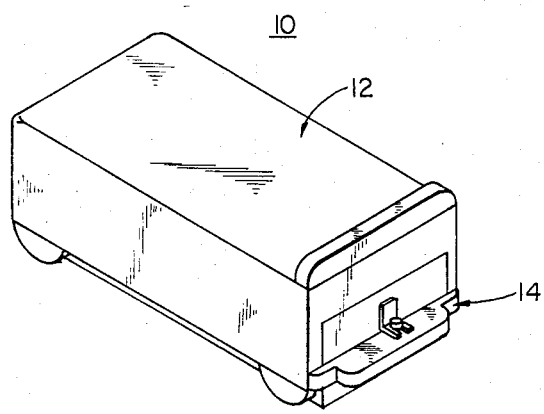
FIG. 1 is an axonometric view of a housing containing the foot pattern device according to this invention.

There is shown in FIG. 1 a foot pattern device 10 according to this invention including a housing 12 with a drawer 14, all made of wood. Drawer 14 is extendible from housing 12 on runners 16, FIG. 2. Drawer 14 includes a cavity 18 having a base 18a and a wall portion 18b, extending upwardly from the base. In cavity 18 on base 18a is foot form 20, which has the general shape of a human foot made in the form of an outline of cork. Foot form 20 may be approximately the same height as wall 18b so that the outline of foot form 20 may be easily located through the deformable sheet when it is in place.

Figure 3:
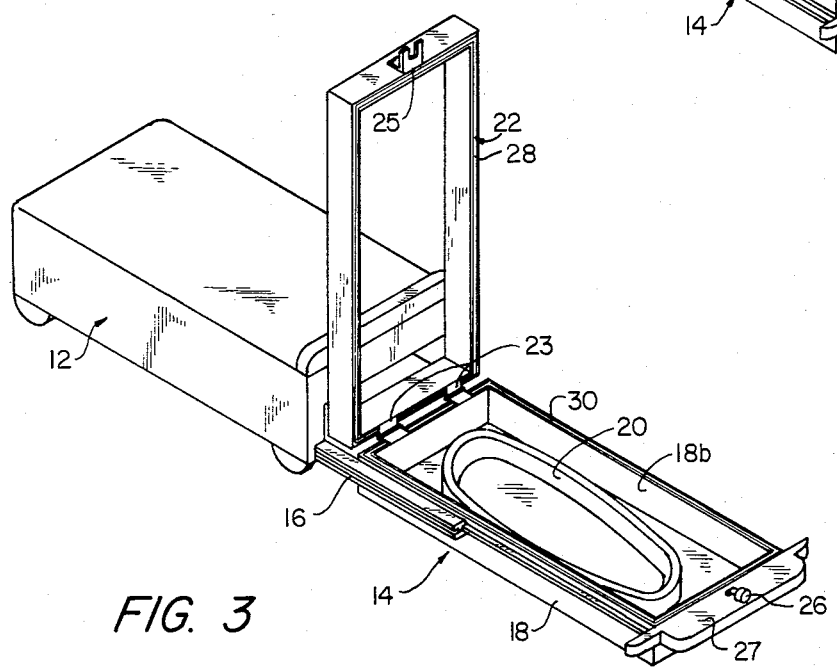
FIG. 3 is a view similar to FIG. 2 with the frame swung open away from the base.

On top of cavity 18 is frame 22, which is secured against wall 18b by means of clamp 24. Frame 22 is swingably connected to cavity 18 by means of hinges 23, along one edge and is secured in position by the latch piece 25 and pin 26, FIG. 3, of clamp 24 on handle 27 at the front of cavity 18. A high-friction material 28, 30 may be applied to either the underside of frame 22 or the top edge of wall 18b where they meet, to provide increased holding power for the sheet of plastic which is to be formed into the shape of the patient's foot.

A heater 40, FIG. 4, is located on the underside of the top of housing 12 and may be connected to a suitable source of electric power by means of switch 42 and line cord 44.

In the beginning of a molding operation, the device 10 appears as shown in FIG. 1. The handle 27 is gripped and the drawer 14 is withdrawn. Clamp 24 is released and frame 22 is swung on hinges 23 up and away from cavity 18. A sheet of plastic is laid on top of wall 18b. Frame 22 is swung back down and clamp 24 is secured to tightly hold the sheet in place. Drawer 14 is then slid back into housing 12 and switch 42 is thrown to energize heater 40. After a short period of time, approximately ninety seconds, when the plastic sheet has softened, the drawer is again withdrawn by means of handle 27 and the patient now places his bare foot or his sock-covered foot on top of the warm deformable sheet 32, FIG. 5, and presses downward, molding the sheet into the shape of his foot as it is pushed into foot form 20. The patient then withdraws his foot from the mold and clamp 24 is released, frame 22 is swung out of the way, and sheet 32 now provides a mold 34, FIG. 6, of the subject's foot.

In cases where it is desirable to introduce a lift or other prosthetic adjustment into the mold, a full lift 50, FIG. 7A, or partial lift 52, FIG. 7B, may be placed within foot form 20.

Other embodiments will occur to those skilled in the art and are within the following claims:

What is claimed is:

1. A foot pattern device comprising:
   a cavity having a base and a wall portion;
   a foot form in said cavity on said base;
   a frame releasably securable to said base for gripping a deformable sheet between the lower edge of said frame and the upper portion of said wall portion;
   means for heating said deformable sheet; and
   clamp means for holding said frame tightly to said wall portion with said deformable sheet between them as a foot is pressed on said warmed deformable sheet into said foot form.

2. The foot pattern device of claim 1 in which said frame is hingeably connected along one edge to said wall portion.

3. The foot pattern device of claim 1 further including a housing for slidably receiving said cavity and frame.

4. The foot pattern device of claim 3 in which said means for heating is disposed in said housing.

5. The foot pattern device of claim 1 in which at least one of the lower edge of said frame and the upper edge of said wall portion where they meet includes a high-friction material for gripping said deformable sheet.

* * * * *